US012575958B1

(12) United States Patent
Nordling et al.

(10) Patent No.: US 12,575,958 B1
(45) Date of Patent: Mar. 17, 2026

(54) ADJUSTABLE LIMB CRADLE FOR POSITIONING OF SURGICAL PATIENTS

(71) Applicant: Arthrex, Inc., Naples, FL (US)

(72) Inventors: Mike Nordling, Hopkinton, MA (US); Jesse Drake, Westborough, MA (US); Justin Mccarthy, Boxborough, MA (US); Loren Crook, Fort Myers, FL (US); Marcela Montoya, Cape Coral, FL (US)

(73) Assignee: Arthrex, Inc., Naples, FL (US)

( * ) Notice: Subject to any disclaimer, the term of this patent is extended or adjusted under 35 U.S.C. 154(b) by 0 days.

(21) Appl. No.: 18/980,625

(22) Filed: Dec. 13, 2024

(51) Int. Cl.
*A61F 5/37* (2006.01)

(52) U.S. Cl.
CPC .............. *A61F 5/37* (2013.01); *A61F 5/3761* (2013.01)

(58) Field of Classification Search
CPC ............. A61M 5/52; A61H 3/02; A61G 1/00; A61G 1/013; A61G 5/125; A61G 13/124; A61G 13/1235; A61G 13/1245; A61G 13/125; A61G 13/128; A61G 13/1285; A61G 13/129; A61F 5/058–05891; A61F 5/37; A61F 5/3715; A61F 5/3723; A61F 5/3761; A61F 5/3769; A61F 5/3776; A61F 5/3792; A61F 5/04; A61F 5/042; A61F 5/048; A61F 5/05
USPC ....................................................... 128/845
See application file for complete search history.

(56) References Cited

U.S. PATENT DOCUMENTS

| | | | | |
|---|---|---|---|---|
| 3,419,002 A | * | 12/1968 | Carmen ................ | A61F 5/0585 602/23 |
| 3,540,719 A | * | 11/1970 | Romney ................. | A61M 5/52 5/503.1 |
| 5,342,288 A | * | 8/1994 | Lee .......................... | A61F 5/048 602/5 |
| 5,628,335 A | * | 5/1997 | Free .......................... | A61H 3/02 135/69 |
| 11,147,730 B2 | | 10/2021 | Moriarty et al. | |
| 2002/0072695 A1 | * | 6/2002 | Doty ..................... | A61F 5/0123 602/5 |
| 2007/0124863 A1 | * | 6/2007 | Kirn ....................... | A61G 13/12 5/646 |
| 2012/0318278 A1 | | 12/2012 | Aboujaoude et al. | |
| 2014/0289965 A1 | * | 10/2014 | Wheeler ................ | A61G 13/12 5/621 |
| 2016/0067080 A1 | * | 3/2016 | Sanders ................ | A61F 5/3761 128/845 |
| 2018/0161193 A1 | * | 6/2018 | Schlesinger ............ | A61F 5/058 |
| 2023/0332738 A1 | | 10/2023 | Glickstein et al. | |

* cited by examiner

*Primary Examiner* — Adam Baker
(74) *Attorney, Agent, or Firm* — Price Heneveld LLP

(57) ABSTRACT

A limb cradle for use in a surgical procedure comprising at least at two sections, wherein at least two of the at least two sections are configured to be attachable to each other, wherein at least two of the at least two sections are configured to be slidable relative to each other so that a length of the limb cradle can be adjusted, and wherein at least one section has at least one connection point onto which a limb positioner may be removably attached.

18 Claims, 10 Drawing Sheets

ADJUSTABLE LIMB CRADLE FOR POSITIONING OF SURGICAL PATIENTS

BACKGROUND

The present invention relates to a support used in positioning a patient's limb for use in surgery, such as shoulder surgeries or any other limb surgeries (e.g., leg surgery).

In shoulder surgeries work is done by the surgeon on the glenohumeral joint. This is a ball-and-socket joint that allows for a wide range of motion of the arm. This joint has more range of motion than any other joint in the body. This joint can be subject to a great deal of stress especially during sports participation and when injured can reduce arm mobility for the patient.

Shoulder surgeons can perform a variety of surgeries on this joint to improve shoulder function, including those that repair tendons, ligaments, cartilage, and other soft tissues. These surgeries can include:

a. Rotator cuff repair: Repairs damage to the rotator cuff, which can be caused by repetitive motion, overhead activities, or traumatic injuries.

b. Arthroscopic rotator cuff repair: Uses small incisions and a camera to repair tendons, ligaments, or cartilage.

c. Arthroscopic repair of the shoulder labrum: Repairs the thick cartilage lining the rim of the joint socket, which can be damaged by dislocation or repetitive stress.

d. Superior capsular reconstruction: Connects the arm bone to the shoulder with grafted tissues.

e. Acromioplasty: Removes bone spurs and part of the acromion to relieve pain.

f. Arthroscopic biceps tenodesis: Detaches and reconnects a torn bicep tendon.

g. Anatomic shoulder replacement: Treats severe arthritis pain by replacing the ball and socket of the joint with artificial parts.

h. Glenohumeral Debridement HemiCap® Resurfacing: A minimally-invasive procedure that removes damaged tissue in the shoulder joint caused by arthritis, overuse, or injury.

The procedures usually require manipulating the arm and the shoulder joint just prior to and during these procedures. Due to this, some shoulder surgical procedures are performed on an anesthetized patient in a sitting or Fowler's position.

Over the last twenty years, limb holders have been developed which can hold the patient's Limb in place and allow the movement of the arm (allowing access to the shoulder joint) during surgery. The arm can be repositioned using these limb holders and then locked into place. Examples of these limb holders include the Spyder Limb Holder (Smith+Nephew) and the Trimano Forte (Arthrex). Both of these limb holders can comprise mechanical limb supports that allow the locking and unlocking of the limb holder and its movement around a plurality of axes. Typically, these limb holders are attached to the surgical table side rail or the side rail of an accessory (such as the Smith+Nephew Beach Chair) or surgical table. These limb holders may be locked and unlocked using a foot pedal thus allowing the surgeon to move the patient's arm into the desired position with the patient's elbow serving as the preferred gripping point.

At the distal end of the limb support there is a connection point whereby a disposable limb cradle can be attached. In the interest of infection control and since the disposable limb cradle is in direct contact with the patient's limb, these cradles are usually single use, are sterilized and are packaged in a sterile pouch.

Some disposable limb cradles used for arms are made or formed of a hard plastic or metal, such as sheet metal, and shaped so that an arm can fit length wise into it. These arm cradles will typically have a foam dressing attached to their upper surface. The foam of the dressing may extend over the edges of the limb cradle and may have a plurality of straps on the underside of the foam that rest on the top surface of the arm cradle. In the case of shoulder surgeries, the foam dressing can thus be "wrapped" around the forearm and the straps can then be tightened to hold the arm in place on the cradle with the foam dressing also protecting the arm.

SUMMARY

Arm cradles may also have a post or protrusion at the distal end so that the patient's hand can be fitted around it for protection. However, some surgeons prefer not to fit the patient's hand around this post in order to avoid placing stress on the hand or fingers.

One issue with these disposable arm cradles is that they are manufactured in a uniform length. Although this length is suitable and usable for many patients those patients with longer forearms may have part of the arm exposed as it hangs off the cradle and this portion of the arm is thus unprotected by the foam dressing or the shell of the cradle, which can result in injuries to the arm.

Another issue is with patients with shorter forearms. Many surgeons will gently grasp the patient's elbow (which sticks out of the proximal end of the arm holder) while positioning the arm. For patients with smaller forearms the elbow may be covered by the disposable arm cradle and not available to the surgeon to grip when positioning the arm and manipulating the shoulder joint. Thus, there is a need for an limb cradle that has an adjustable length to accommodate the wide variety of patient forearm lengths.

Additionally, there is a need for a limb cradle that has a post or protrusion that can be removably attached. This can allow surgeons who do not want the patient's hand positioned around the post to remove the post prior to using the device.

The present invention provides a limb cradle, such as an arm cradle, that may consist of two or more sections onto which a post or a protrusion may be removably attached.

The arm cradle may be formed out of a suitable material including hard plastic, metal or injection molded materials including acrylonitrile butadiene styrene (ABS), polyethylene (PE), polycarbonate (PC), polyamide (PA), polypropylene (PP), polystyrene (PC), acrylic (PMMA), or other suitable materials.

In some embodiments the arm cradle may be formed of two or more sections.

In other embodiments the arm cradle may have at least two sections including at least a first section and at least a second section with the arm resting on a portion of the upper surface of each of the section.

In one embodiment the first section may be formed with slight curvature of the surface around a central axis. The slight surface curvature in some embodiments may conform to the shape of a patient's arm.

The first section may have rectilinear channels formed along its sides that are open at the distal end. These rectilinear channels may have slots formed along its outer walls in one embodiment.

In one embodiment the first section has a connection point formed into its proximal end which allows it to be removably attached to a limb holder The distal end of the first section of the arm cradle may have a semi-circular cut out formed.

There may be a tab formed into and through and located near the midline of the center surface of the second section in some embodiments. This tab may in turn have a detent formed into the center region of its bottom surface.

The bottom surface of the first section may have a series of small indents formed near and along its midpoint that are in general alignment with the tab with a detent formed into it center of the second section in one embodiment.

The proximal end of the second section of the arm cradle may be sized such that it will slide into the rectilinear channels formed along the edges of the first section at its distal end, thereby adjusting the length of the arm cradle to accommodate different arm sizes.

The second section of the arm cradle may have at least two protrusions formed into and sticking out from the proximal edge of the second section. These protrusions may be bifurcated and may have one or more small barbs formed along the inside edges of the proximal end of the bifurcations The distal end of the second section may be formed as a semi-circle. In the middle of this semi-circle may be formed a through hole into which for a hand gripping post may be removably attached.

The protrusions with barbs of the second section may be slid into the opposing channels formed along the length of the outside edges of the first section. The small barbs on the protrusion of the second section may be removably fitted into slots form into the outer wall of the channel formed along the edges of the first section.

It can be seen that the second section may be fitted into the first section with a slip fit. A tab may be formed into and through the surface of the second section. The tab may have a detent formed near its center proximal region. The tab may be angled so that this detent interfaces with indents formed into the center region of the bottom surface of the first section. When the sections are moved relative to one another, the tab detent clicks into one of the indents formed into the bottom surface of the first section. The first and second sections may be slid into one another shortening the overall length of the limb cradle or slid away from one another lengthening the limb cradle to accommodate different limb sizes. The tab detent interacts with the indents in the top surface of the first section to lock the sections in place along with the barbs of the second section that are removably fit into the fitment slots formed into the outer channel formed into the opposing edges of the first section.

The post may be formed of a suitable material such as metal or plastic. The post can be formed such that it can be removably fitted into through hole formed though distal region of the second section.

A connection point can be formed into and towards the distal region of the first section of the upper section. The connection point can be fashioned such that it allows the arm cradle to be removably attached to a limb holder. The upper surface of the of the first section may have a strip of hook and loop fabric attached thereto located near the midpoint and center of this section.

An arm dressing can be formed with a strip of hook and loop attached to the bottom surface of the dressing. It can be sized and located so that it mates with the strip of hook and lop fabric attached to the top surface of the first section of the arm cradle.

The arm dressing may have a plurality of foam flaps and flexible straps attached to its under surface. The foam may be open cell or memory foam. The straps may be formed of nylon or other flexible materials. In some embodiments straps can be removably attached to features formed in the first section of the arm cradle. In some embodiments two foam flaps may be attached to opposing sides on the bottom surface of the arm dressing and be of sufficient length to overlap one another when wrapped around the top surface of the arm dressing when an arm is in place.

A limb cradle for use in a surgical procedure comprises at least at two sections, wherein at least two of the at least two sections are configured to be attachable to each other, wherein at least two of the at least two sections are configured to be slidable relative to each other so that a length of the limb cradle can be adjusted, and wherein at least one section has at least one connection point onto which a limb positioner may be removably attached.

The limb cradle can include at least one of the at least two sections has at least one removably attached post, a foam wrap configured to be attachable to at least one of the at least two sections, wherein the foam wrap can include at least one connecting strap.

Another limb cradle for use in a surgical procedure can comprise at least two sections, wherein the at least two sections are configured to be attachable to each other, and wherein at least two of the at least two sections are configured to be slidable relative to each other so that a length of the limb cradle can be adjusted.

In this limb cradle, at least one section of the at least two sections can have at least one connection point to which a limb positioner may be removably attached.

Another limb cradle for use in a surgical procedure can comprise at least at two sections, wherein a portion of the at least two sections are configured to be fitted into to each other, wherein at least two of the at least two sections are slidable relative to each other so that a length of the limb cradle can be adjusted, and wherein at least one of the of the at least two sections has at least one connection point to which a limb positioner may be removably attached.

In this limb cradle, at least one of the at least two sections can have at least one removably attachable post.

In this limb cradle, at least one of the at least two sections can have a tab with at least one detent on its bottom surface and wherein at least one of the at least one detents is co-linear with at least two indents formed on a top surface of a second section.

This limb cradle can further include a foam wrap configured to be attachable to at least one section of the at least two sections.

In this limb cradle, the foam wrap can include at least one connecting strap.

Another limb cradle for use in a surgical procedure can comprise at least at two sections, wherein a portion of the at least two sections may fit into to each other, wherein at least two of the at least two sections may slide relative to each other along a plane so that a length of the limb cradle can be adjusted, and wherein at least one of the at least two sections has at least one connection point to which a limb positioner may be removably attached.

In this limb cradle, at least one section of the at least two sections can have at least one removably attached post.

In this limb cradle, a first section can have a tab with at least one detent on its bottom surface and wherein the at least one detent is co-linear with at least two indents formed on a top surface of a second section.

This limb cradle can further include a foam wrap configured to be attachable to at least one of the least two sections.

In this limb cradle, the foam wrap can have at least one connecting strap.

Another limb cradle for use in a surgical procedure can comprise at least two sections, wherein a portion of at least two sections may fit into to each other, and wherein at least two of the at least two sections are slidable relative to each other along a plane so that a length of the limb cradle can be adjusted; wherein at least one section of the at least two sections has at least one connection point to which a limb positioned may be removably attached, and wherein at least one section of the at least two sections has at least one removably attached post.

In this limb cradle, at least one section of the at least two sections can have a tab with at least one detent on its bottom surface and wherein the at least one detent is co-linear with at least two indents formed on the top surface of a second section.

This limb cradle can further include a foam wrap configured to be attachable to at least one of the at least two sections.

In this limb cradle, the foam wrap can have at least one connecting strap.

Another limb cradle for use in a surgical procedure comprises at least two sections, wherein the at least two sections may be attached to each other, wherein a portion of at least two sections may fit into to each other; wherein at least two sections may slide relative to each other along a plane so that a length of the limb cradle can be adjusted, wherein at least one of the sections has at least one connection point to which a limb positioner may be removably attached, wherein at least one section has at least one removably attached post.

Another limb cradle for use in a surgical procedure comprises at least at two sections, wherein the at least two sections have at least one top, one bottom and four side surfaces, wherein the at least two sections may be attached to each other, wherein a portion of at least two sections may fit into to each other, and wherein at least two sections may slide relative to each other along a plane so that a length of the limb cradle can be adjusted, wherein at least two sections may be slid into the other, wherein at least one of the sections has at least one connection point to which a limb positioned may be removably attached, and wherein at least one section has at least one removably attached post.

In this limb cradle, the first section has two channels formed on opposing sides of the first section; and the second section has two opposing prongs formed at an end portion of the second section configured to be slidably fit into a respective one of the two channels to thereby change the length of the arm cradle.

This limb cradle can further comprise barbs are formed at ends of the opposing prongs; and a plurality of fit slots are formed in outer walls of the two channels into which the barbs can be removably fit to thereby change a length of the arm cradle.

In this limb cradle, the second section can have a hole formed therein configured to receive the post, wherein the hole includes a cutout sized to fit a snap protuberance formed on a distal end surface of the post.

In this limb cradle, a plurality of strap slots can be formed in formed in slot protrusions formed in outside walls of the channels, wherein the strap slots are configured to secure securement straps to secure a foam wrap to the limb cradle.

Another limb cradle for use in a surgical procedure can comprise at least at two sections, wherein at least two of the at least two sections are configured to be attachable to each other, wherein at least two of the at least two sections are configured to be slidable relative to each other so that a length of the limb cradle can be adjusted, and wherein at least one section includes a mount point having a through hole formed therein, the through hole being configured to receive a mount pin.

In this limb cradle, the mount pin can be configured to be fitted into the through hole and secured on a side of the at least one section by a threaded lug.

In this limb cradle, the mount pin can include a threaded hole formed therein and sized to accept the threaded lug.

DETAILED DESCRIPTION

Figure 1:
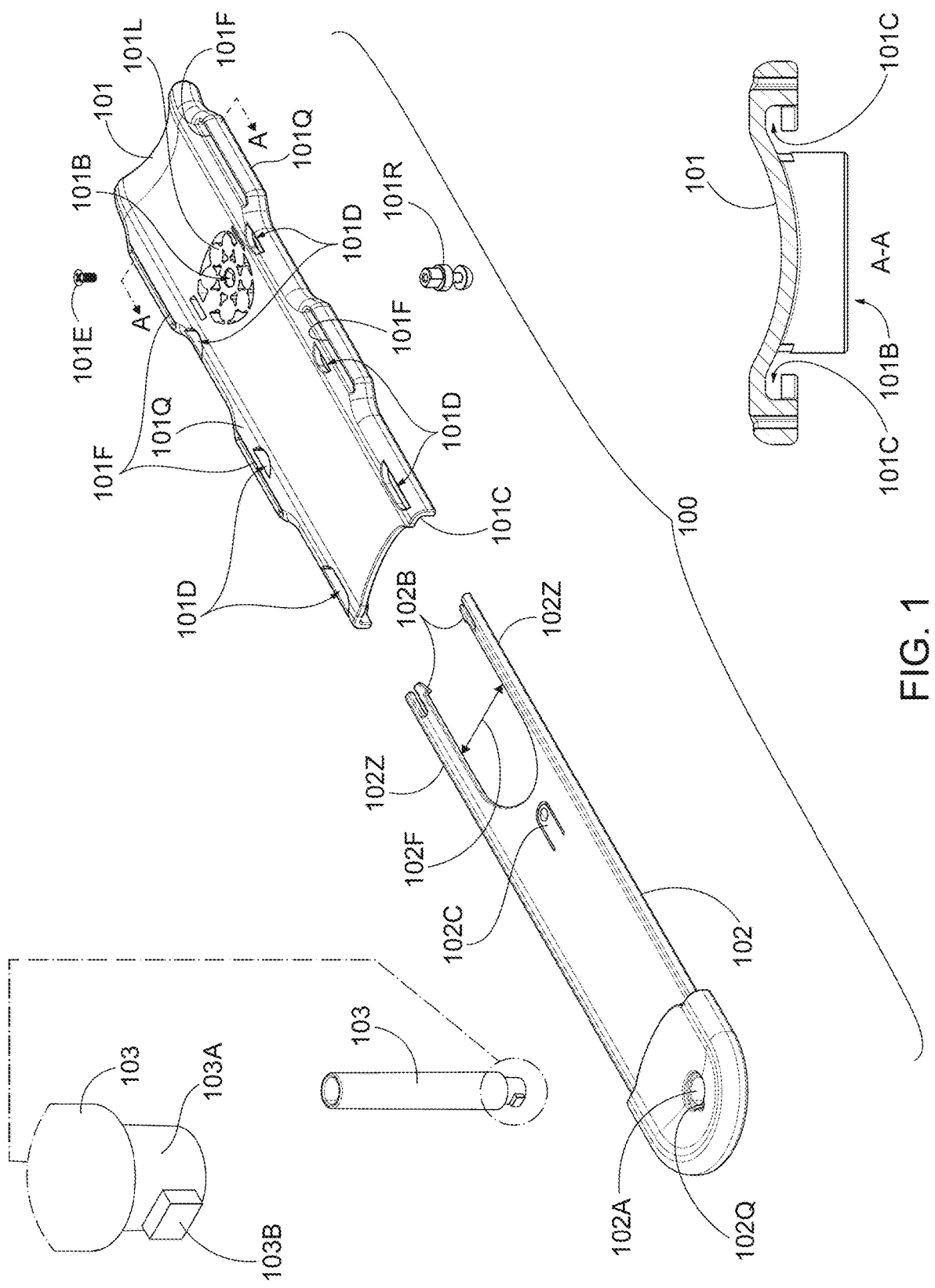
FIG. 1 illustrates perspective top and side views and a sectional view of at least one embodiment of the invention.

FIG. 1 illustrates a top perspective view some aspects of one embodiment of limb cradle, such as arm cradle 100 including second section 102 with hole 102A formed through its distal region and with tab 102C formed through it top surface in its proximal region. Cut out 102F has opposing prongs 102Z formed which oppose each other with barbs 102B formed at its proximal region. Hole 102A has cutout 102Q sized to fit snap protuberance 103B formed on the surface of distal portion 103A of post 103, which can be used to removably secure post 103 to first section 101. First section 101 has channel 101C formed on each side (see Section A-A). Fit slots 101D are formed through the outer wall of channel 101C. Strap slots 101F are formed into and through the outer wall of channel 101C. Mount point 101L has hole 101B formed therethrough. Mount pin 101R has threaded hole 101T formed in its top end (see FIG. 2) sized to accept threaded lug 101E which is sized to fit snugly in through hole 101B formed into and through mount point 101L

Figure 2:
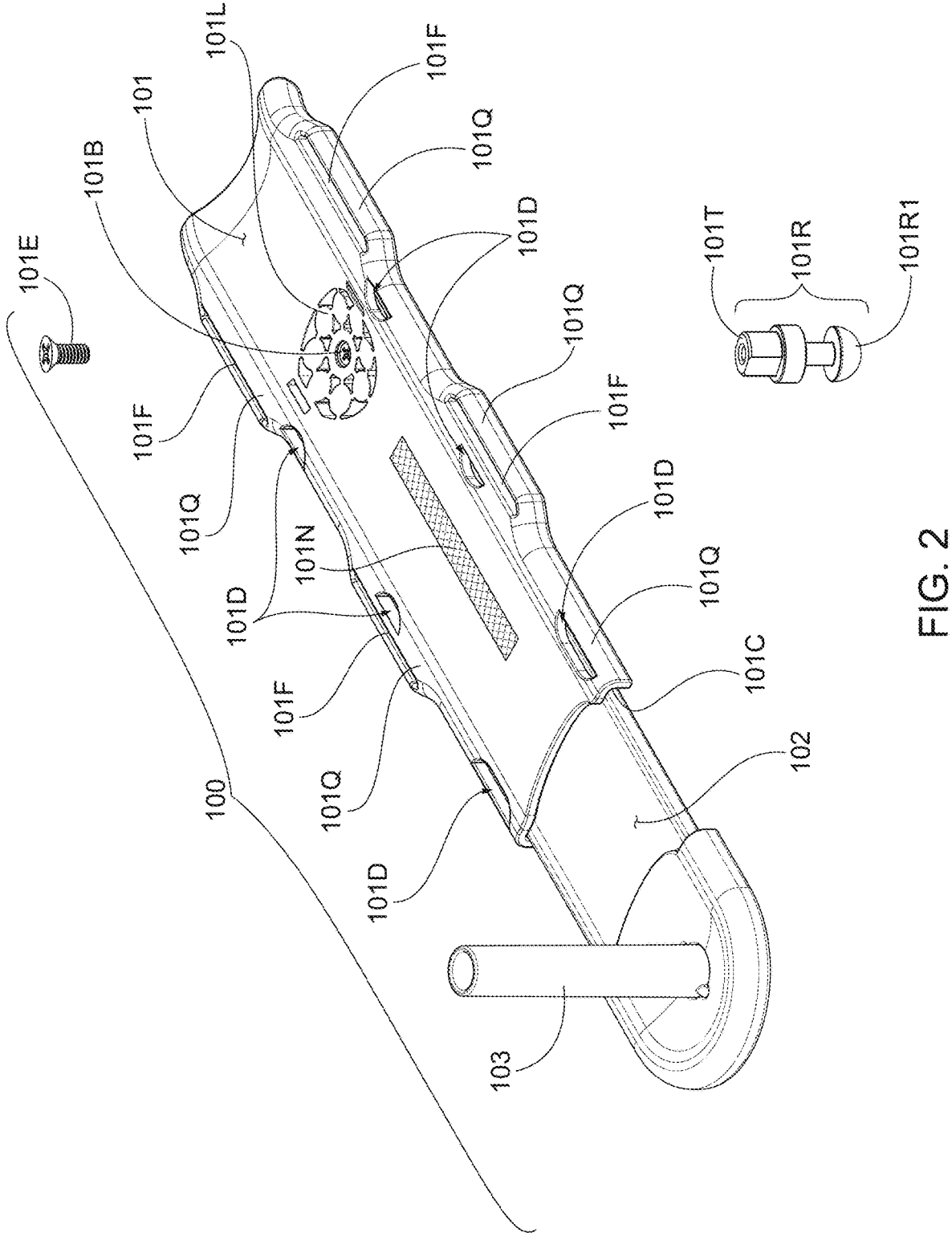
FIG. 2 illustrates a top perspective view.

FIG. 2 illustrates another perspective top view of the one embodiment of the limb cradle 100. Post 103 with fit snap protuberance 103B (see FIG. 1) snap fits into hole 102A (not shown, see FIG. 1) formed through distal portion of second section 102. Prongs 102Z (not shown, see FIG. 1) of second section 102 are fitted into channels 101C. Prongs 102Z have barbs 102B (not shown, see FIG. 1) which can be removably fitted into fit slots 101D formed through the outer wall of channel 101C. Strap slots 101F are formed into the outer surface of channel 101C. Mount point 101L has through hole 101B formed through its top surface which can extend to its bottom surface. Mount pin 101R has threaded hole 101T formed into its top portion sized to accept threaded lug 101E. In this illustration second section 102 is being slid into channels 101C of first section 101. The first and second sections 101/102 may be slid into one another thereby shortening the overall length of the arm cradle 100, or slid away from one another thereby lengthening the arm cradle so that different arm sizes can be accommodated in the limb cradle. The first section 101 can include a hook or loop fabric strip 101N that is configured to adhere to a corresponding hook or loop fabric strip 109T on arm dressing 109, as described below.

Figure 3:
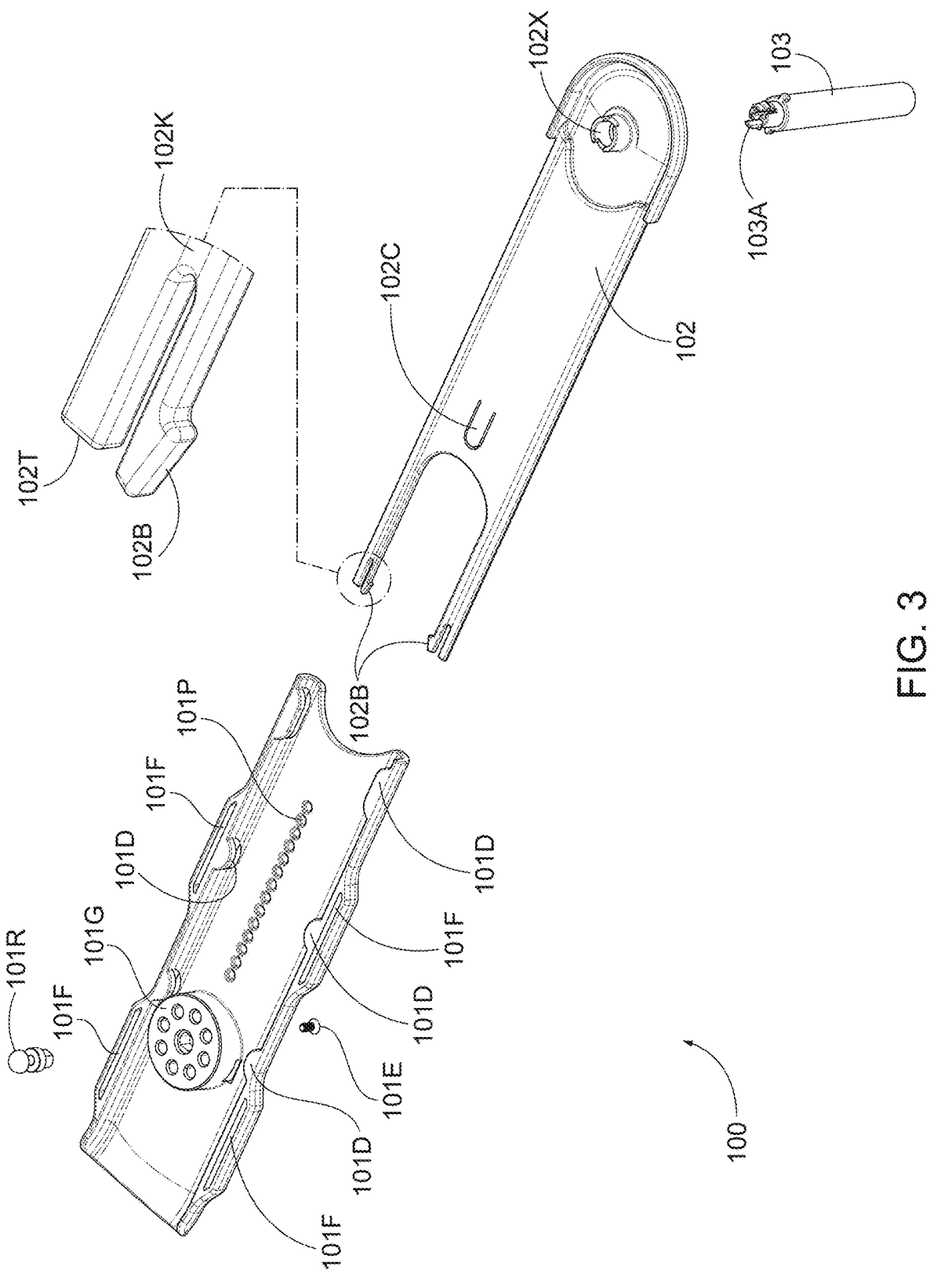
FIG. 3 illustrates a bottom perspective view of some aspects of at least one embodiment of the invention.

FIG. 3 illustrates a bottom perspective view and some details of an embodiment of the disclosure including first section 101 and second section 102 of limb cradle 100. Second section 102 has a through hole 102X formed into its bottom surface near an end portion of the second section 102. is sized to accept post 103 with snap fit protrusion 103B. Post 103 is placed in through hole 102X on the top surface of second section 102 (not shown, bottom surface is illustrated here in FIG. 3) and fitted therein (see FIG. 1). Indents 101P can be formed on the center line of the bottom surface of first section 101 in this embodiment. Mount puck 101G can be formed on the bottom surface of first section 101 and protrudes outwardly from this surface. The mount puck 101G is designed to fit into a support arm (not shown), such Trimano support arm, in order to support the limb cradle 100 during surgery. Mount pin 101R can be fitted into hole formed into and through mount hole 101B to secure the mount puck 101G to a support arm. The mount puck 101G can include a plurality of holes 101G1, for example 8 holes, formed therein that are configured to mate with a plurality of outdents, for example 4, formed in the support arm in order secure the mount puck to the support arm. The orientation of the limb holder 100 relative to the support art can be changed by rotating the limb holder and mount puck 101G relative to the support arm and mating the holes 101G1 with different outdents. For example, having 8 holes 101G1 and 4 indents allows rotation in 45 degree increments.

Channel 101C (see FIG. 1 and FIG. 2) are formed along opposing sides (edges) of first section 101 and is sized to accept prongs 102Z which are formed on opposing sides of second section 102. Proximal area of Section 102 has prongs 102Z formed on its outside edges with guide section 102T formed into its distal inside edges. Barbs 102B along with guide section 102T are sized to fit into fit slots 101D formed into the outer side wall of channel 101C. Strap slot protrusions 101Q with a slots 101F are formed therein are formed into the outer wall of channel 101C. Bottom surface of second section 102 has a tab 102C formed therein. Through hole 102X is formed in the distal end of the second section 102 and is sized so that the distal end 103A of post 103 of will fit into it. 101. As shown in FIG. 3, a detent can be formed in the bottom surface of the second section 102 that extends from the through hole 102X. This detent can be used to lock the post 103 to the second section 102. Alternatively, the post can be mounted to the second section 102 without using a detent so that the post does not extend from the bottom section of the second section 102.

Figure 4:
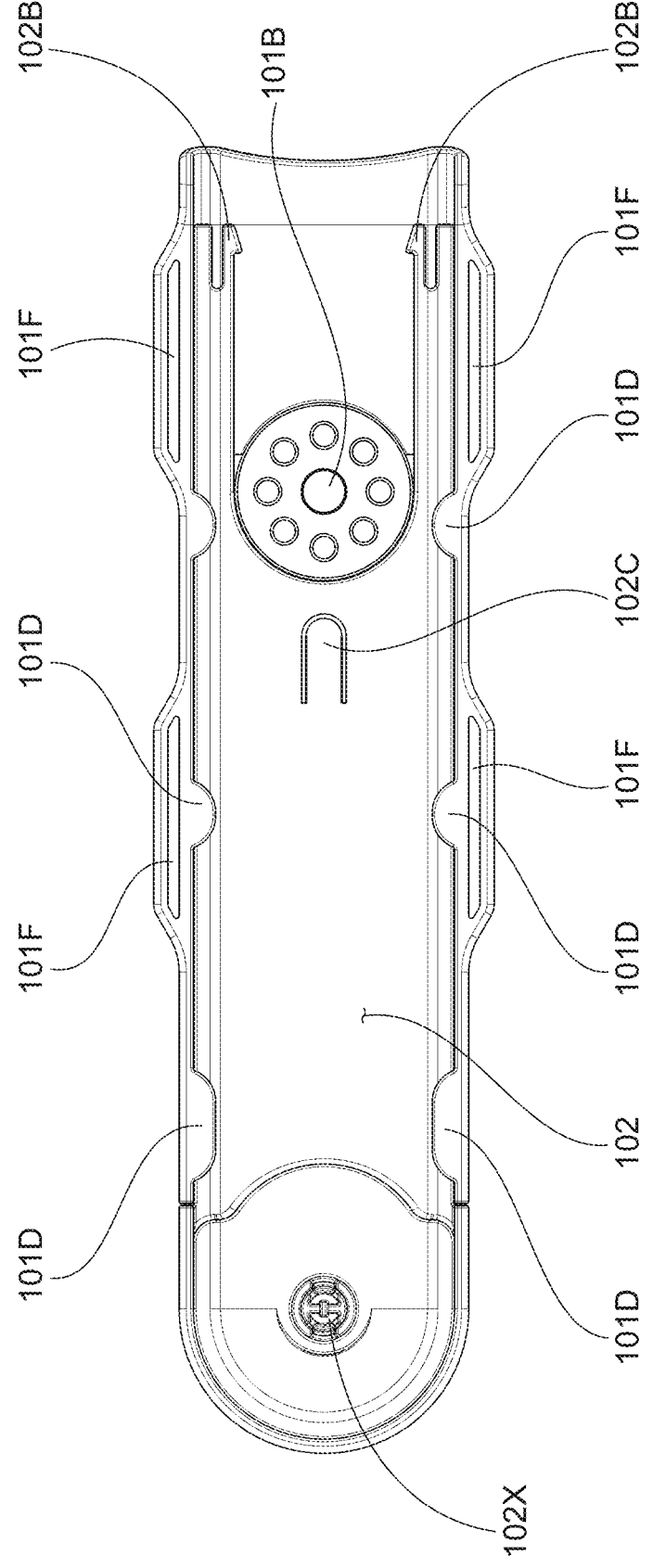
FIG. 4 illustrates a bottom view of one aspect of at least one embodiment of the invention.

FIG. 4 illustrates a top view of some aspects of one embodiment of limb cradle 100. Hole 101X is formed into the distal section of first section 101. First section 101 is fitted into second section 102 by sliding the proximal end of section 102 with guide section and barbs 102B (not shown, see FIG. 3) into channels 101C (not shown, see FIG. 3) such that barbs 102B (not shown, see FIG. 3) are snap fitted into the fit slots 101D formed into the outside wall of channel

101C (not shown, see FIG. 1 and FIG. 3). This sliding of the first section 101 into and out of second section 102 adjusts the overall length of the limb cradle 100 so that different limb sizes can be accommodated in the limb cradle 100. Strap mounts 101F with strap slot protrusions 101Q are formed into the outer wall of channel 101C (not shown see FIG. 3).

Figure 5:
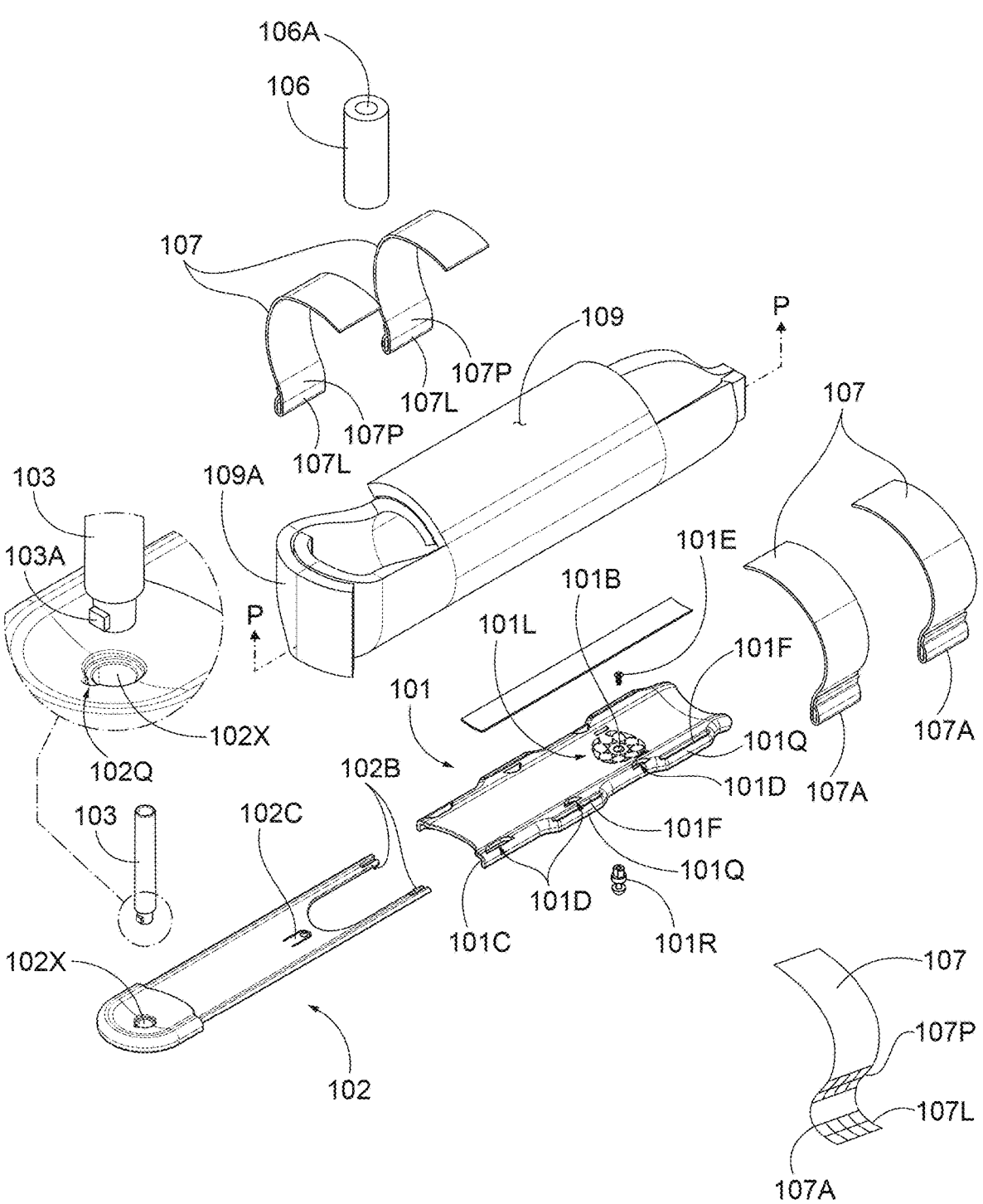
FIG. 5 illustrates certain details including a perspective view of some elements of the disclosure.

FIG. 5 illustrates a top perspective exploded view of the limb cradle 100 including first section 101, second section 102, foam limb protector 109, straps 107, post 103 and foam post wrap 106. First section 101 has channel 101C formed on it opposing edges. Channel 101C has fit slots 101D formed into its outer (lateral) walls. Slot protrusions 101Q are formed into the outer wall of channel 101C and have slots 101F formed through its lateral edges. Mount point 101L (also see FIG. 1) is formed into a top surface of first section 101 and has through hole 101B formed through its surface for receiving mount pin 101R, which can be passed into through hole 101B from a bottom surface of first section 101. Mount pin 101R has threaded hole 101T formed into its top surface (see FIG. 2) and round mount 101R1 formed in the opposing end. Threaded lug 101E may be passed through through hole 101B formed in top surface of first section 101 and secured into threaded hole 101T formed into top surface of mount pin 101R in order to secure the mount pin 101R to the first section 101. First section 102 has prongs 102Z formed into its proximal end with barbs 102B formed at ends of the prongs. Tab 102C can be formed into and through the surface of second section 102. Through Hole 102X is formed into the distal region of second section 102 and is sized to accept post 103. This through hole 102X can have cut out 102Q formed into a portion of its outer circumference sized to accept snap fit protrusion 103B formed into the circumference of distal end 103A which projects out from one end of post 103. Foam wrap 109 may be constructed of open cell foam and may be sized to wrap around a variety of limb sizes. Foam post wrap 106 has hole 106A formed therein and is sized to fit over post 103. Securement strap 107 can include hook and loop sections 107P and 107L. Hook section 107P and loop section 107P are attached to an outer distal end of strap 107. Strap 107 may be formed of flexible material such as woven fabric or flexible rubber/plastic. Mount pin 101R has threaded hole 101T formed in its top end sized to accept threaded lug 101E which is sized to fit snuggly in hole 101B formed into and through mount point 101L. Through hole 101B is formed into and through mount point 101L. Hole 102A has cutout 102Q sized to fit snap protuberance 103B formed on the surface of distal end 103A of post 103.

Figures 6A, 6B:
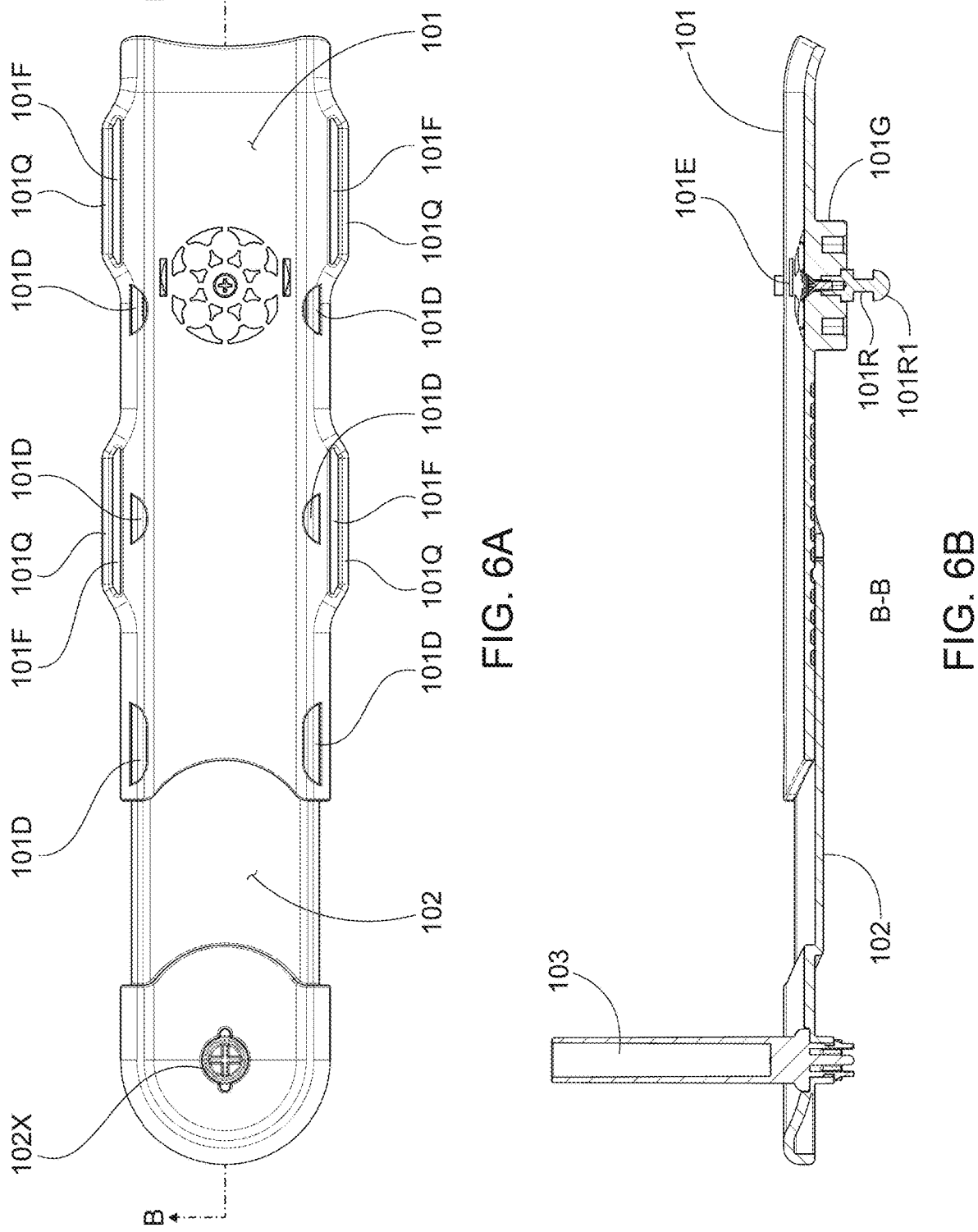
FIGS. 6A and 6B illustrate a top and a sectional view of at least one embodiment of the invention.

FIG. 6A and FIG. 6B illustrate a top view and a sectional view, respectively, of some aspects of one embodiment of arm cradle 100. The top view illustrates first section 101 fitted into second section 102 (see FIG. 1 and FIG. 3). First section 101 has a plurality of fit slots 101D formed into the outer wall of channel 101C (not shown, see FIG. 1 and FIG. 3.). Strap slot protrusions 101Q are formed into the outer wall of channel 101C and have strap slots 101F formed through their lateral edges. Distal end of second section 102 has through hole 102X formed therein sized to accept one end of post 103. Mount point 101L (see FIG. 1) has a hole 101B formed at a top portion thereof (not shown, see FIG. 2) into which mount knob 101R may be fitted. Threaded lug 101E may be screwed into threaded hole 101T (not shown, see FIG. 2) formed into end of mount pin 101R.

Figure 7:
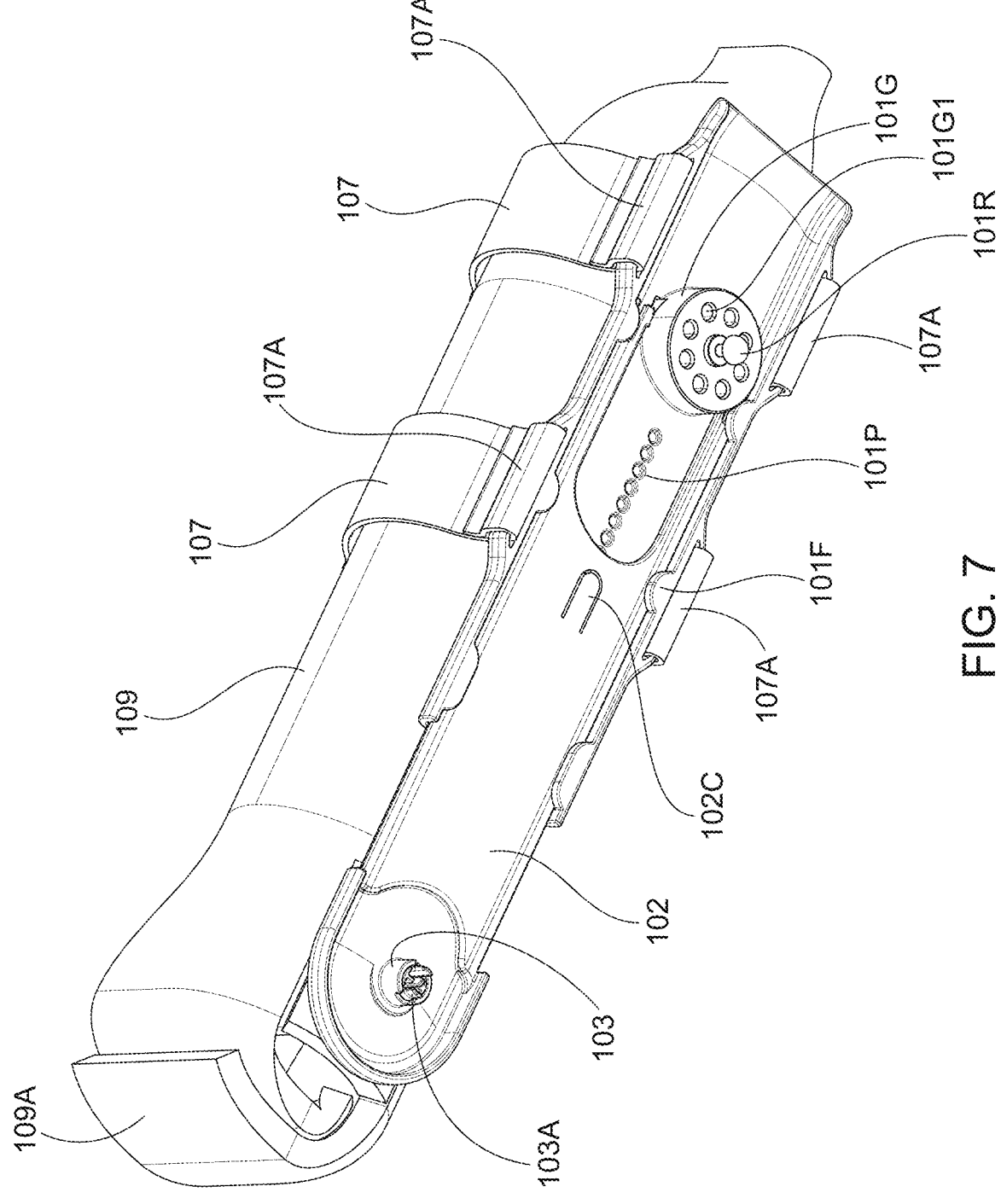
FIG. 7 illustrates a bottom sectional view of some aspects of at least one embodiment of the invention.

FIG. 7 illustrates a bottom perspective view of one embodiment of the disclosure in which first section 101 is fitted into second section 102 with outer edges of second section 102 fitted into channel 101C. Tab 102C can be formed into the distal center and bottom region of second section 102. First section 101 has indents 101P formed into its center and bottom region which are aligned with the tab 102C formed in bottom surface of second section 102. The tab 102C may have a detent formed near its center proximal region. The tab 102C may be angled so that the detent interfaces with the indents 101P formed into the center region of the bottom surface of the first section. When the first and second sections are moved relative to one another, the tab detent clicks into one of the indents 101P formed into the bottom surface of the first section 101. The first and second sections may be slid into one another shortening the overall length of the limb cradle or slid away from one another lengthening the limb cradle to accommodate differ- ent limb sizes. The detent of tab 102C interacts with the indents 101P in the top surface of the first section 101 to temporarily lock the first and second sections in place along with the barbs 102B of the second section 102 that are removably fit into the fit slots 101D formed into the outer channel formed into the opposing edges of the first, as presented above. The indents 101P and tab 102C detent can act as a ratcheting system that can allow the first and second sections to move relative to one another in increments equal to the spacing of the indents 101P.

Straps 107 are fitted through strap slots (not shown, see FIG. 1 and FIG. 3) formed in strap slot protrusions 101Q formed in the outside wall of channel 101C of first section 101. Strap end 107A of securement strap 107 is sized to fit into a strap slot 101F (not shown) formed in strap slot protrusions 101Q which are formed in the outer wall of channel 101C. Strap 107 can be fitted around foam wrap 109 thereby securing it to limb cradle 100. Hand wrap section 109A can be attached to foam wrap 109 at the distal end of limb cradle 100. Mount pin 101R is fitted into hole 101B and secured on the other side of first section 101 by threaded lug 101E (not shown, see FIG. 1, FIG. 2 and FIG. 6B).

Figure 8:
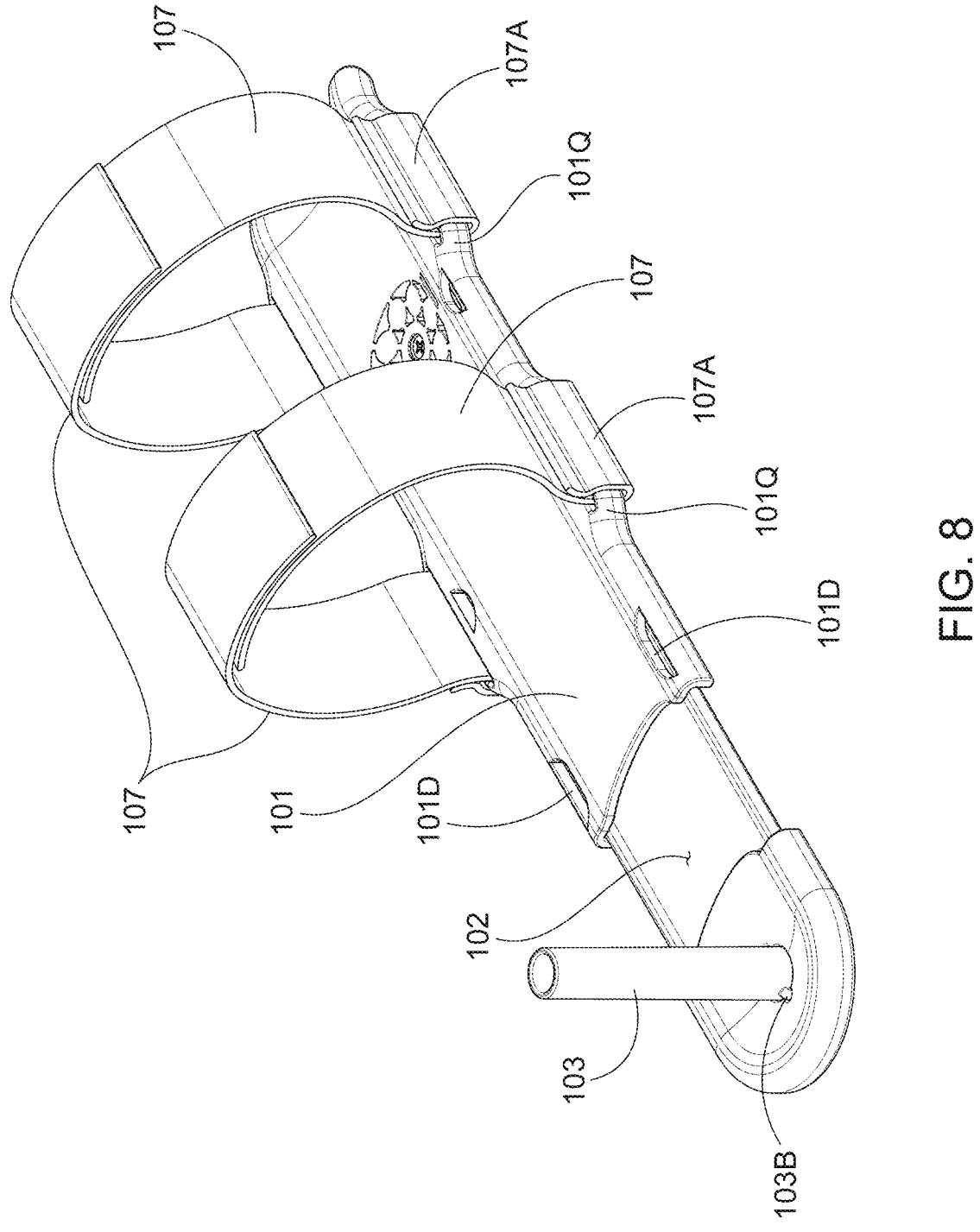
FIG. 8 illustrates a top perspective view of one embodiment of the disclosure.

FIG. 8 illustrates a top perspective view of one embodi- ment of the disclosure whereby first section 101 is mated with second section 102 with outer edges of second section 102 removably fitted into channels 101C formed in first section 100. Straps 107 are fitted through strap slots 101F (not shown, see FIG. 1 and FIG. 3) formed in slot protru- sions 101Q formed in the outside wall of channel 101C of first section 101. Strap end 107A of securement strap 107 is sized to fit into a strap slot 101F (not shown) formed in slot protrusions 101Q which are formed in the outer wall of channel 101C. Strap 107 can be fitted around foam wrap 109 thereby securing it to limb cradle 100. Hand wrap section 109A (not shown, see FIG. 7) can be attached to foam wrap 109 at the distal end of limb cradle 100.

Figure 9:
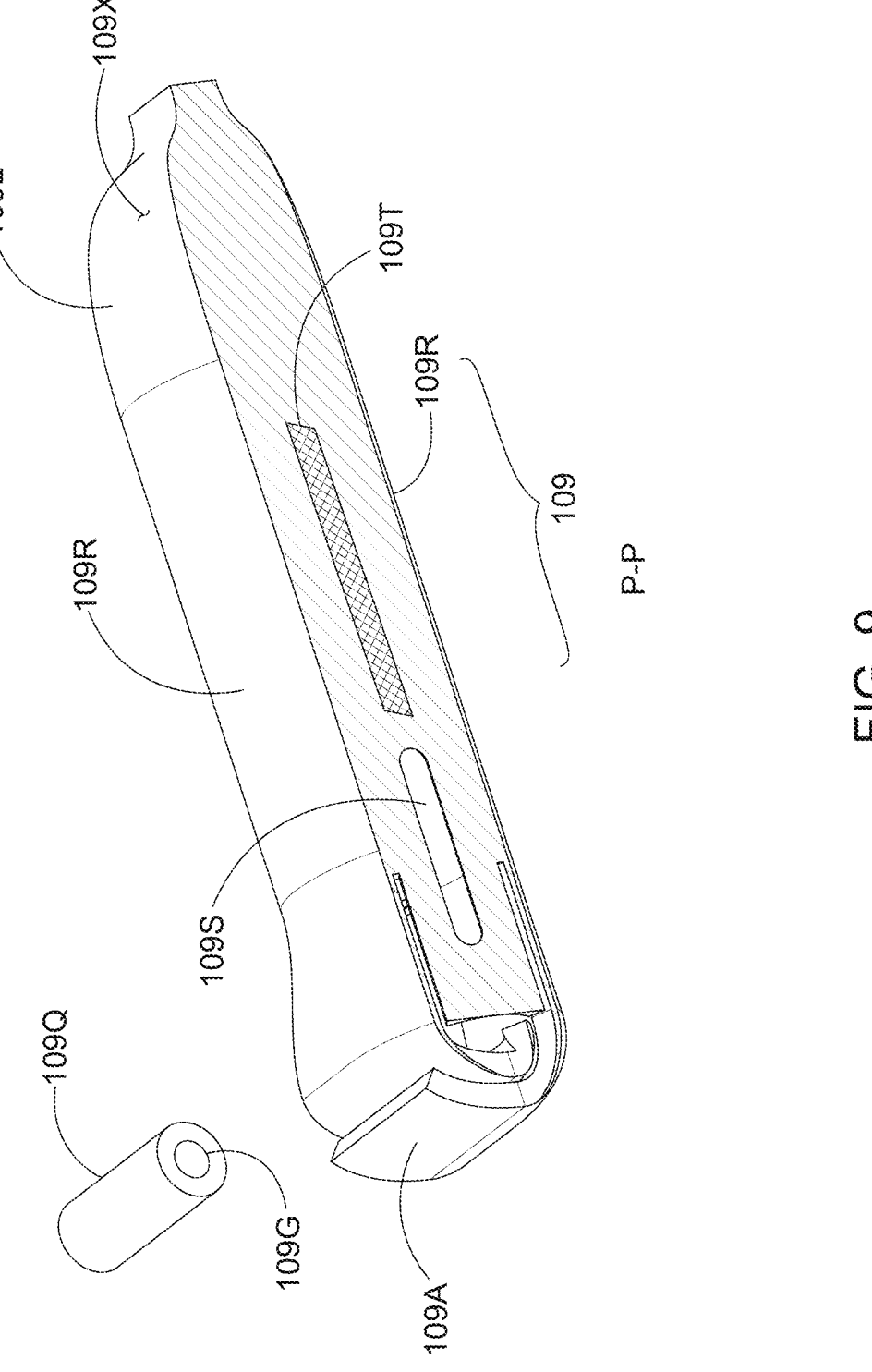
FIG. 9 illustrates a bottom perspective view of some aspects the arm dressing.

FIG. 9 illustrates a bottom perspective view of some aspects of one embodiment of the disclosure, specifically the arm dressing 109. FIG. 9 illustrates section view P-P from FIG. 5. Arm dressing 109 has bottom surface 109X and sides 109L with flaps 109R attached to bottom surface 109X. Hook or loop fabric strip 109T is attached near the mid center point of bottom surface 109X. The hook or loop fabric strip 109T of arm dressing 109 can be mounted to a corresponding hook or loop fabric strip 101N mounted on section 101 (see FIG. 2). Slot 109S is formed into and through the distal region and midpoint region of bottom surface 109X. Foam cylinder 109Q has hole 109G formed therein and is sized to fit over post 103 (not shown, see FIG. 2).

Figure 10:
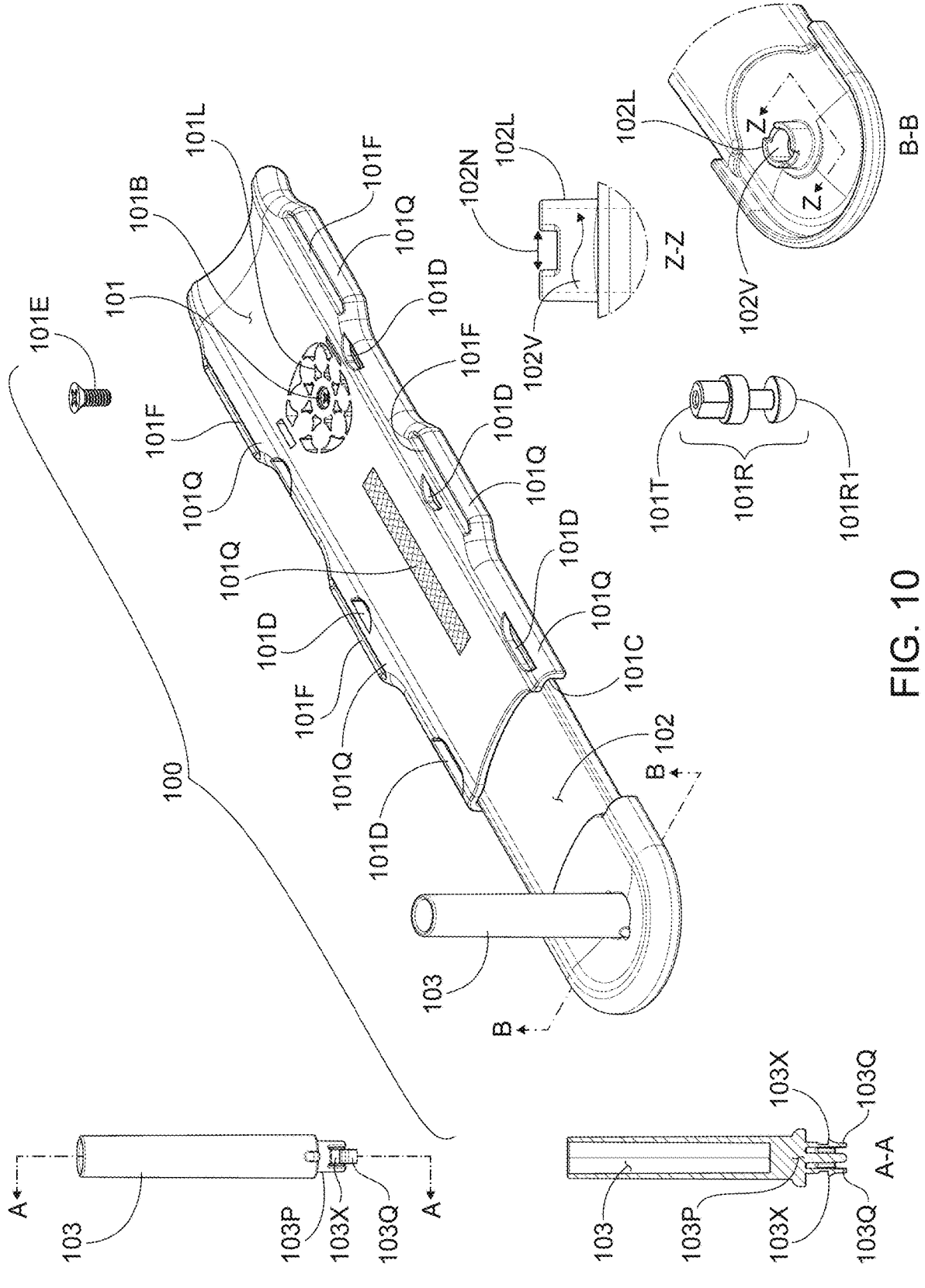
FIG. 10 illustrates a perspective top and side views and a sectional view of another embodiment of the invention.

FIG. 10 illustrates another perspective top view of another embodiment of the limb cradle 100. Specifically, FIG. 10 shows the knob 103 having forks 103Q that extend from a proximal end thereof. The forks 103Q include a snap fit protuberance 103X formed into a side portion thereof. The knob 103 also includes fit forks 103P extending from the proximal end of the knob 103, as shown in FIG. 10. Second section 102 has through hole 102V formed through its distal region. Ring 102L is formed around through hole 102V on the bottom side of second section 102 as shown in FIG. 9. Ring 102L has notch cutouts 102N formed on it opposing sides as shown in FIG. 9. The snap fit protuberances 103X are configured to snap into the notch cutouts 102N of ring 102L when the proximal end of knob 103 is slid into and through hole 102V.

Those having ordinary skill in the art will appreciate that various changes can be made to the above embodiments without departing from the scope of the invention.

The above detailed description refers to the accompany- ing drawings. The same or similar reference numbers may have been used in the drawings or in the description to refer to the same or similar parts. Also, similarly named elements may perform similar functions and may be similarly designed, unless specified otherwise. Details are set forth to provide an understanding of the exemplary embodiments. Embodiments, e.g., alternative embodiments, may be prac- ticed without some of these details. In other instances, well known techniques, procedures, and components have not been described in detail to avoid obscuring the described embodiments.

The foregoing description of the embodiments has been presented for purposes of illustration only. It is not exhaus- tive and does not limit the embodiments to the precise form disclosed. While several exemplary embodiments and fea- tures are described, modifications, adaptations, and other implementations may be possible, without departing from the spirit and scope of the embodiments. Accordingly, unless explicitly stated otherwise, the descriptions relate to one or more embodiments and should not be construed to limit the embodiments as a whole. This is true regardless of whether or not the disclosure states that a feature is related to "a," "the," "one," "one or more," "some," or "various" embodi- ments. As used herein, the singular forms "a," "an," and "the" may include the plural forms unless the context clearly dictates otherwise. Further, the term "coupled" does not exclude the presence of intermediate elements between the coupled items. Also, stating that a feature may exist indi- cates that the feature may exist in one or more embodiments.

In this disclosure, the terms "include," "comprise," "con- tain," and "have," when used after a set or a system, mean an open inclusion and do not exclude addition of other, non-enumerated, members to the set or to the system. Further, unless stated otherwise or deducted otherwise from the context, the conjunction "or," if used, is not exclusive, but is instead inclusive to mean and/or. Moreover, if these terms are used, a subset of a set may include one or more than one, including all, members of the set.

Further, if used in this disclosure, and unless stated or deducted otherwise, a first variable is an increasing function of a second variable if the first variable does not decrease and instead generally increases when the second variable increases. On the other hand, a first variable is a decreasing function of a second variable if the first variable does not increase and instead generally decreases when the second variable increases. In some embodiment, a first variable may be an increasing or a decreasing function of a second variable if, respectively, the first variable is directly or inversely proportional to the second variable.

The disclosed systems, methods, and apparatus are not limited to any specific aspect or feature or combinations thereof, nor do the disclosed systems, methods, and apparatus require that any one or more specific advantages be present or problems be solved. Any theories of operation are to facilitate explanation, but the disclosed systems, methods, and apparatus are not limited to such theories of operation.

Modifications and variations are possible in light of the above teachings or may be acquired from practicing the embodiments. For example, the described steps need not be performed in the same sequence discussed or with the same degree of separation. Likewise various steps may be omitted, repeated, combined, or performed in parallel, as necessary, to achieve the same or similar objectives. Similarly, the systems described need not necessarily include all parts described in the embodiments, and may also include other parts not described in the embodiments. Accordingly, the embodiments are not limited to the above-described details, but instead are defined by the appended claims in light of their full scope of equivalents. Further, the present disclosure is directed toward all novel and non-obvious features and aspects of the various disclosed embodiments, alone and in various combinations and sub-combinations with one another.

While the present disclosure has been particularly described in conjunction with specific embodiments, many alternatives, modifications, and variations will be apparent in light of the foregoing description. It is therefore contemplated that the appended claims will embrace any such alternatives, modifications, and variations as falling within the true spirit and scope of the present disclosure.

What is claimed is:

1. A limb cradle for use in a surgical procedure comprising:
   at least two sections comprising a first section and a second section;
   wherein the first section and the second section are configured to be attachable to each other; and
   wherein the first section and the second section are configured to be slidable relative to each other so that a length and a surface area of a top surface of the limb cradle can be adjusted, and wherein the first section has two channels formed on opposing sides of the first section, each channel being formed along a length of the first section, and wherein the second section has two opposing prongs formed at an end portion of the second section configured to be slidably fit into a respective one of the two channels.

2. The limb cradle of claim 1, wherein at least one of the at least two sections has at least one removably attached post.

3. The limb cradle of claim 1, further including a foam wrap configured to be attachable to at least one of the at least two sections.

4. The limb cradle of claim 3, wherein the foam wrap includes at least one connecting strap.

5. The limb cradle of claim 1, wherein at least one section of the at least two sections has at least one connection point onto which a limb positioner may be removably attached.

6. The limb cradle of claim 1, wherein at least one of the at least two sections has a tab with at least one detent on its bottom surface and wherein at least one of the at least one detents is co-linear with at least two indents formed on a top surface of an other section of the at least two sections.

7. A limb cradle for use in a surgical procedure comprising:
   at least two sections comprising a first section and a second section;
   wherein a portion of the first section and the second section are configured to fit into to each other;
   wherein the first section and the second section are slidable relative to each other along a plane so that a length and a surface area of a top surface of the limb cradle can be adjusted;
   wherein at least one section of the at least two sections has at least one connection point to which a limb positioner may be removably attached;
   wherein at least one section of the at least two sections has at least one removably attached post; and
   wherein the first section has two channels formed on opposing sides of the first section, each channel being formed along a length of the first section, and wherein the second section has two opposing prongs formed at an end portion of the second section configured to be slidably fit into a respective one of the two channels.

8. The limb cradle of claim 7, wherein at least one section of the at least two sections has a tab with at least one detent on its bottom surface and wherein the at least one detent is co-linear with at least two indents formed on a top surface of an other section of the at least two sections.

9. The limb cradle of claim 7 further including a foam wrap configured to be attachable to at least one of the at least two sections.

10. The limb cradle of claim 9, wherein the foam wrap has at least one connecting strap.

11. A limb cradle for use in a surgical procedure comprising:
   at least two sections comprising a first section and a second section;
   wherein the first section and the second section are configured to be attachable to each other;
   wherein a portion of the first section and the second section are configured to fit into to each other;
   wherein the first section and the second section are configured to slide relative to each other along a plane so that a length and a surface area of a top surface of the limb cradle can be adjusted;
   wherein at least one of the sections has at least one connection point to which a limb positioner may be removably attached;
   wherein at least one section has at least one removably attached post; and
   wherein the first section has two channels formed on opposing sides of the first section, each channel being formed along substantially a length of the first section, and wherein the second section has two opposing prongs formed at an end portion of the second section configured to be slidably fit into a respective one of the two channels.

12. A limb cradle for use in a surgical procedure comprising:
   at least two sections comprising a first section and a second section;
   wherein the at least two sections have at least one top, one bottom and four side surfaces;
   wherein the first section and the second section are configured to be attached to each other;
   wherein a portion of the first section and the second section are configured to fit into to each other;
   wherein the first section and the second section are configured to slide relative to each other along a plane so that a length and a surface area of a top surface of the limb cradle can be adjusted;

wherein at least one of the sections has at least one connection point to which a limb positioner may be removably attached;

wherein the at least one section has at least one removably attached post; and wherein the first section has two channels formed on opposing sides of the first section, each channel being formed along a length of the first section, and wherein the second section has two opposing prongs formed at an end portion of the second section configured to be slidably fit into a respective one of the two channels.

13. The limb cradle of claim 12, wherein:

barbs are formed at ends of the opposing prongs; and a plurality of fit slots are formed in outer walls of the two channels into which the barbs can be removably fit to thereby change the length of the top surface.

14. The limb cradle of claim 12, wherein the second section has a hole formed therein configured to receive the post, wherein the hole includes a cutout sized to fit a snap protuberance formed on a distal end surface of the post.

15. The limb cradle of claim 12, wherein a plurality of strap slots are formed in formed in slot protrusions formed in outside walls of the channels, wherein the strap slots are configured to secure securement straps to secure a foam wrap to the limb cradle.

16. The limb cradle of claim 12, wherein at least one section includes a mount point having a through hole formed therein, the through hole being configured to receive a mount pin.

17. The limb cradle of claim 16, wherein the mount pin is configured to be fitted into the through hole and secured on a side of the at least one section by a threaded lug.

18. The limb cradle of claim 17, wherein the mount pin includes a threaded hole formed therein and sized to accept the threaded lug.

* * * * *